United States Patent [19]

Delsing

[11] Patent Number: 5,214,966
[45] Date of Patent: Jun. 1, 1993

[54] METHOD AND APPARATUS FOR MEASURING MASS FLOW

[76] Inventor: Jerker Delsing, Kungsljusvägen 56, S-241 20 Löddeköpinge, Sweden

[21] Appl. No.: 678,983
[22] PCT Filed: Oct. 31, 1991
[86] PCT No.: PCT/SE89/00615
  § 371 Date: Apr. 29, 1991
  § 102(e) Date: Apr. 29, 1991
[87] PCT Pub. No.: WO90/05283
  PCT Pub. Date: May 17, 1990

[30] Foreign Application Priority Data

Oct. 31, 1988 [SE] Sweden ............... 8803925

[51] Int. Cl.$^5$ .............................................. G01F 1/66
[52] U.S. Cl. ............................. 73/861.28; 73/861.27
[58] Field of Search .......... 73/861.28, 861.27, 861.26, 73/861.02, 861.03, 32 A, 24.05

[56] References Cited

U.S. PATENT DOCUMENTS

| | | | |
|---|---|---|---|
| 2,911,825 | 11/1959 | Kritz | 73/861.03 |
| 2,959,054 | 11/1960 | Welkowitz | 73/861.26 X |
| 3,283,574 | 11/1966 | Roth | 73/861.26 X |
| 3,958,447 | 5/1976 | Baker et al. | 73/861.02 X |
| 4,015,470 | 1/1977 | Morrison | 73/32 A X |
| 4,195,517 | 1/1980 | Kalinoski et al. | 73/861.27 |
| 4,320,659 | 5/1982 | Lynnworth et al. | 73/589 |
| 4,462,261 | 7/1984 | Keyes et al. | 73/861.27 X |
| 4,748,857 | 6/1988 | Nakagawa | . |
| 4,885,938 | 12/1989 | Higashi | 73/861.02 |
| 4,930,358 | 6/1990 | Motegi et al. | 73/861.28 |

FOREIGN PATENT DOCUMENTS

| | | |
|---|---|---|
| 2437107 | 2/1976 | Fed. Rep. of Germany ... 73/861.28 |
| 3016323 | 11/1980 | Fed. Rep. of Germany . |
| 3013482 | 10/1981 | Fed. Rep. of Germany . |
| 0896418 | 1/1982 | U.S.S.R. ............... 73/861.28 |

Primary Examiner—Herbert Goldstein
Assistant Examiner—Elizabeth L. Shopbell
Attorney, Agent, or Firm—Kane, Dalsimer, Sullivan, Kurucz, Levy, Eisele and Richard

[57] ABSTRACT

In a method for measuring the mass flow M of a fluid flowing through a pipe having a cross-sectional area A, the sound velocity $c_2$ in the fluid is determined as well as the flow velocity v of the fluid by sing-around technique. Further, reflection technique is used which comprises measuring the amplitude both of an ultrasonic pulse which has been reflected in a boundary between a first and a second material having different acoustic impedances, and of an ultrasonic pulse which has been reflected in the boundary between the second material and the fluid, it being possible to determine the density of the fluid on the basis of the measured amplitudes, the sound velocity $c_2$ in the fluid and the acoustic impedances of the first and the second material. The mass flow M is then obtainable as $M = v \times A \times \rho_2$. A mass flowmeter especially has a transducer with a piezoelectric crystal (5), a first block (6) of a first material disposed adjacent said crystal, and a second block (7) of a second material disposed between the first block and the fluid, and calculating and amplitude metering means (10 and 12).

9 Claims, 1 Drawing Sheet

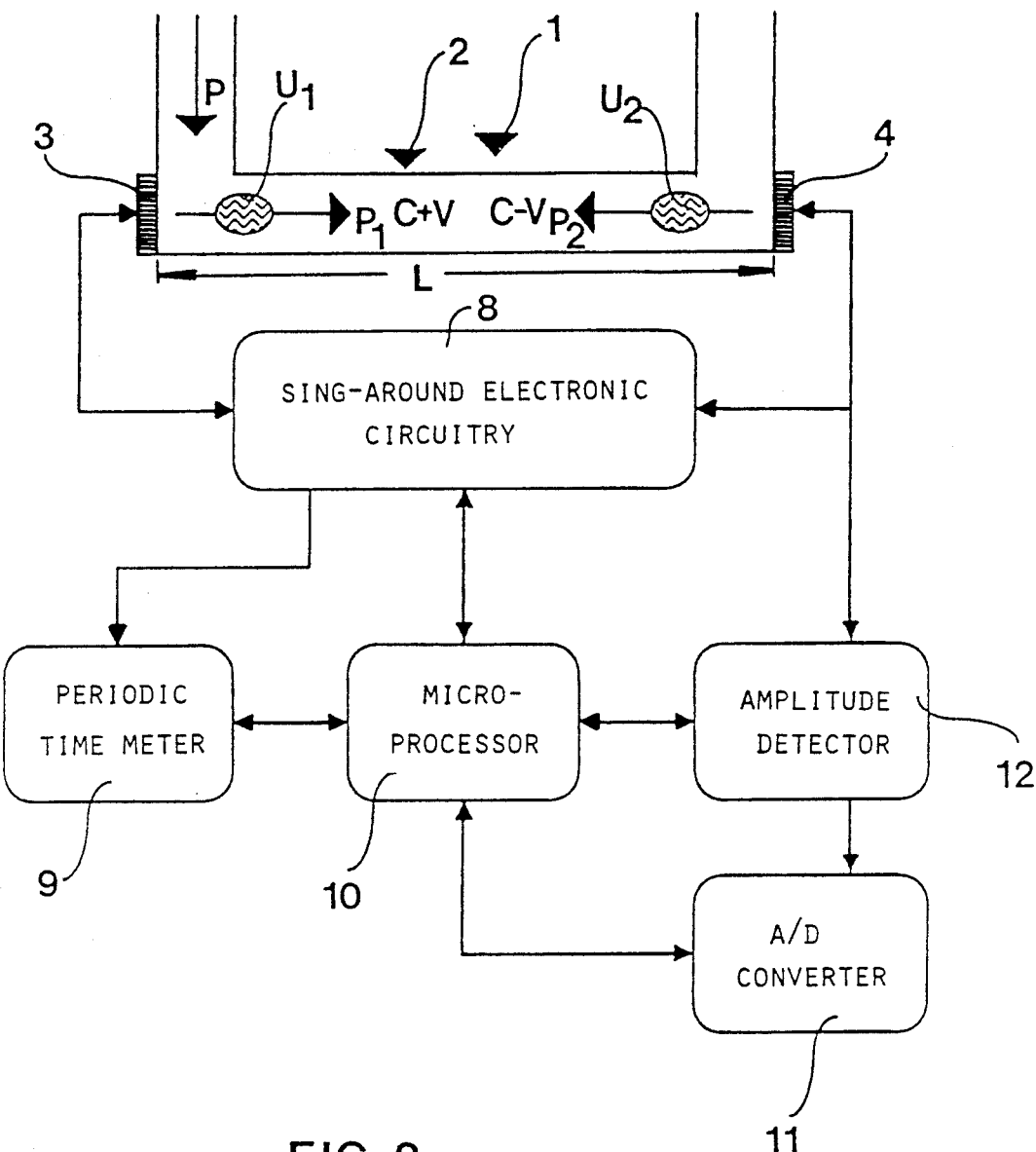
FIG._1
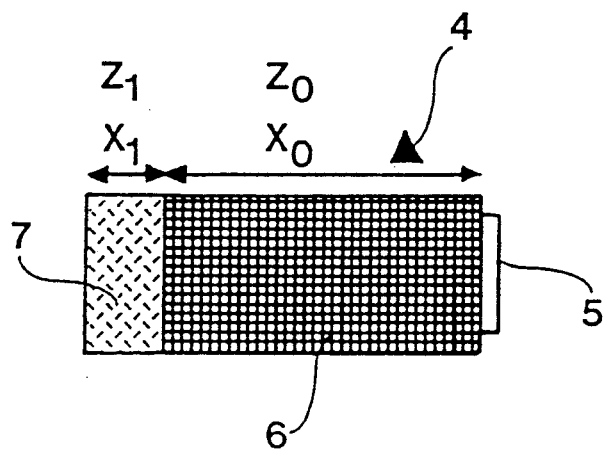
FIG._2

METHOD AND APPARATUS FOR MEASURING MASS FLOW

The present invention relates to a method for measuring mass flow. The invention also relates to an apparatus for carrying out the method.

Fluid flow, i.e. liquid and gas flow, is one of the most important and most frequently used measuring parameters for controlling and monitoring industrial processes. There is thus a considerable need for simple and reliable measuring techniques and apparatuses having high measuring accuracy.

A fluid flow can be measured either as a volume flow ($m^3/s$) or a mass flow (kg/s). In general, the volume flow is easier to measure, but in many contexts it is of greater interest to measure the mass flow since the mass is a fundamental characteristic which, unlike volume, does not vary with pressure and temperature. In e.g. fuel supply control in aircraft it is thus the mass of the fuel supplied, and not the volume, that determines which speed can be achieved.

Today, there are two main types of mass flowmeters, viz. meters directly measuring the mass flow rate and meters in which the density and the flow velocity of the fluid are measured separately, the mass flow M being determinable as $$M = \rho \times A \times v$$

where $\rho$ is the density of the fluid, A is the cross-section of the pipe through which the fluid flows, and v is the flow velocity of the fluid.

In industry, use was made until quite recently, primarily of mass flowmeters of the first main type relying on the law of conservation of momentum for direct measurement of mass flow. This meter was however of complex design and expensive. Moreover, it obstructed the fluid flow, causing a pressure drop and loss of energy. In recent years, this type of meter has therefore in many cases been superseded by another meter for direct measurement of mass flow, namely the Coriolis meter, which causes only a limited pressure drop of the fluid.

One type of Coriolis meter comprises a U-shaped pipe with fixedly mounted ends, and a mechanical tuning fork causing the pipe to perform sinusoidal mechanical oscillations about a position of equilibrium. The fluid is caused to flow through the oscillating pipe, each moving element of the fluid being subjected to a Coriolis force which in one leg of the U-pipe is directed in one sense and in the other leg of the U-pipe in the opposite sense. The result is a moment of force tending to rotate the U-pipe. The amount of rotation is measured in this case by two optical detectors, giving the mass flow as $$M = K \times \Delta t$$

where K is a constant and $\Delta t$ is the time interval from the point of time one detector is passed by one leg of the U-shaped pipe to the point of time the other detector is passed by the other leg of the pipe.

As compared with the momentum meter, the Coriolis meter is advantageous in that the fluid is subjected to only a small pressure drop, but also the Coriolis meter is an expensive and mechanically complex meter. Another disadvantage of these two techniques is that both meters contain movable parts, which places high demands on the materials used in the meters.

An apparatus which is of the other main type and has no movable parts is disclosed in U.S. Pat. No. 2,911,825. This apparatus measures the flow velocity v of a fluid flowing through a pipe by sing-around technique. To this end, the apparatus comprises a first pair of piezoelectric crystals which are mounted opposite each other, each on one side of the pipe, and one of which is adapted to transmit acoustic waves in a first direction in the fluid and the other of which is adapted to receive these waves, and a second pair of similarly mounted piezoelectric crystals transmitting and receiving, respectively, acoustic waves in another direction in the fluid. The two crystals of each pair are interconnected by a feedback path consisting of an amplifier and a wave packet generator which is triggered to transmit wave packets to the transmitting crystal when the amplifier is receiving waves from the receiving crystal. The repetition frequency $f_1$ of the wave packet in the first path will be proportional to $c - v \cos \theta$, where c is the sound velocity in the fluid, v the flow velocity of the fluid, and $\theta$ the angle between the flow velocity and the direction of the waves in the fluid. Similarly, the repetition frequency $f_2$ of the wave packets in the second path will be proportional to $c + v \cos \theta$. A circuit connected to the feedback paths forms the difference $f_2 - f_1$, which thus is proportional to the flow velocity v of the fluid.

In the apparatus described, the density b of the fluid is further determined by determining the acoustic impedance Z of the fluid. To this end, the apparatus comprises a further piezoelectric crystal which is mounted in the pipe wall, an inductor and an oscillator. When the crystal has been tuned to resonance, the voltage drop across the crystal is substantially proportional to the acoustic impedance Z of the fluid, i.e. to $c \times \rho$.

The determination of the density $\rho$ relies on the fact that the frequency $f_1$ is proportional to $c - v \cos \theta$ and that v is small compared with c. In U.S. Pat. No. 2,911,825, v is therefore neglected, and $f_1$ is considered substantially proportional to c. The mass flow rate then is obtainable as $M = v \times c \times \rho \rho c$.

The apparatus described in U.S. Pat. No. 2,911,825 however suffers form several shortcomings, the most serious being the difficulty to achieve high measuring accuracy. The reason for this is, for example, that the sound velocity c in the fluid is determined in an inaccurate manner and that it is not properly considered that the sensitivity of the crystal for determining the acoustic impedance of the fluid varies with temperature and because of ageing. Besides, inaccuracies may occur if the two feedback paths are not adequately matched to each other or if they are not at the same temperature. A further shortcoming of this apparatus is that it requires as many as five piezoelectric crystals.

One object of the present invention is to provide a method for measuring the mass flow of a fluid, which is based on the principle of separately measuring the flow velocity of the fluid and its density, and which gives more accurate results than prior art methods based on the same principle.

Another object is to provide a method for measuring the mass flow, in which the influence of the measuring environment on the measurement is considered.

A further object of the invention is to provide an apparatus for carrying out the method.

Yet another object of the invention is to provide an apparatus which requires a smaller number of transducers as compared with known apparatuses.

These objects are achieved by a method and an apparatus having the features recited in the appended claims.

The method and the apparatus according to the invention rely on sing-around technique for accurately determining both the sound velocity in the fluid and the flow velocity thereof. The same equipment is here used for measurements both in the cocurrent direction of the fluid and in the countercurrent direction thereof, the systematic errors becoming the same for both directions, which means greater measuring accuracy Concurrently with the determination of the flow velocity and the sound velocity, the acoustic impedance of the liquid is determined, it being taken into consideration that the sensitivity of the transducer employed varies, inter alia, with the ambient temperature. This measuring technique gives very high accuracy since all parameters which may vary with the measuring environment are measured. For measuring the mass flow according to the invention, only two piezoelectric transducers are required, at least one of which is specially designed for density measurement.

One embodiment of the present invention will now be described with reference to the accompanying drawing, in which FIG. 1 schematically shows a mass flowmeter according to the invention, and FIG. 2 shows a transducer adapted to determine the density of a fluid and included in the apparatus shown in FIG. 1.

As shown in FIG. 1, the measurements with the apparatus according to the present invention can be carried out in a U-shaped pipe 1 connected to the pipe or conduit through which the fluid to be subjected to measurements is flowing. The pipe section 2 extending between the legs of the U-pipe 1 has a known cross-sectional area A and a known length L between the outer walls of the legs. In the following description, is assumed that the fluid is flowing through the U-pipe 1 in the direction indicated by the arrow P.

The apparatus for mass flow measurements according to the invention comprises a first ultrasonic transducer 3 disposed in the upstream end of the pipe section 2, and a second ultrasonic transducer 4 disposed in the downstream end of the pipe section 2 opposite the first transducer 3, such that the distance between the two transducers is L. Each of the two transducers 3, 4 has a piezoelectric crystal acting as transmitter and receiver of ultrasonic pulses. Further, and as shown in FIG. 2, one transducer 4 is specially designed for measuring the density of the fluid. To this end, the transducer 4 comprises, in addition to a piezoelectric crystal 5, a first block 6 of a material having an acoustic impedance $Z_0$ and a length $x_0$, and a second block 7 having an acoustic impedance $Z_1$ and a length $x_1$. The two blocks 6, 7 are disposed in such a manner that an ultrasonic pulse transmitted from the crystal 5 will traverse the two blocks 6, 7 before reaching the fluid, the first block 6 being disposed between and in contact with the crystal 5 and the second block 7, and the second block 7 is disposed between and in contact with the first block 6 and the fluid.

As shown in FIG. 1, the two transducers 3, 4 are interconnected by a sing-around electronic circuitry 8. The sing-around technology is well-known to those skilled in the art. Thus, the contents of the box 8 in FIG. 1 will not be described in more detail here, it being sufficient to point out that it contains means for generating and transmitting electric pulses to the two transducers 3, 4, and means for receiving electric pulses from these transducers.

The sing-around electronic circuitry 8 further is connected to a periodic time meter 9 connected to a microprocessor 10. The microprocessor 10 is connected to the sing-around electronic circuitry 8, to an A/D converter 11 and to an amplitude detector 12. In addition to being connected to the microprocessor 10, the amplitude detector 12 is connected to the ultrasonic transducer 4, the sing-around electronic circuitry 8 and the A/D converter 11. All circuits shown in the block diagram of FIG. 1 are known to those skilled in the art and commercially available.

In the following description, it will be explained how the mass flow is measured by means of the present invention. The microprocessor 10 emits a start signal to the sing-around electronic circuitry 8 generating an electric excitation signal. This signal is supplied to the ultrasonic transducer 3 converting it into an ultrasonic pulse which is transmitted into the fluid in the cocurrent direction thereof, as indicated by the arrow $P_1$. The ultrasonic pulse $U_1$ travels through the fluid at a velocity $c+v$, where c is the sound velocity in the fluid and v is the flow velocity of the fluid, and is received by the second ultrasonic transducer 4 converting the ultrasonic pulse $U_1$ into an electric signal which is passed on to the sing-around electronic circuitry 8. When receiving the signal from the ultrasonic transducer 4, the sing-around electronic circuit 8 generates an excitation signal which is transmitted to the ultrasonic transducer 3, and a signal which is transmitted to the periodic time meter 9. The above-described method of transmitting and receiving signals is repeated until the microprocessor 10 emits a stop signal to the sing-around electronic circuitry 8 after a predetermined number N of repetitions.

The periodic time meter 9 is used for determining the periodic time, i.e. the time it takes a pulse to traverse the distance L in the fluid. The periodic time is determined by the periodic time meter 9 summing the number N of signals from the sing-around electronic circuitry 8, measuring the time $T_1$ passing between the start and stop signals from the microprocessor 10 and dividing this time $T_1$ by the number N of pulses. The periodic time thus determined is supplied to the microprocessor 10 and stored in a memory therein.

Alternatively, the periodic time meter 9 may be used for determining the periodic time by measuring, a certain number of times, the time passing from the point of time the sing-around electronic circuitry 8 emits a signal to the point of time it again receives the same signal, summing these times and determining the mean thereof.

When the periodic time for the cocurrent direction has been determined, the steps described above are repeated for the countercurrent direction of the fluid in order to determine the periodic time for this direction. The sing-around electronic circuitry 8 thus generates an electric signal supplied to the ultrasonic transducer 4 converting the signal into an ultrasonic pulse $U_2$ which, as indicated the arrow $P_2$, moves in the countercurrent direction of the fluid at a velocity $c-v$. The ultrasonic pulse $U_2$ is received by the ultrasonic transducer 3 and passed on to the sing-around electronic circuitry 8. In the same way as for the cocurrent direction, the periodic time meter 9 determines the periodic time for the counter-current direction and supplies it to the microprocessor 10.

On the basis of the periodic times, the microprocessor 10 then calculates the flow velocity v of the fluid according to the formula $$v = L(N/T_1 - N/T_2)/2 \cos\theta$$

where L, as stated above, is the distance between the two ultrasonic transducers 3 and 4, and also the sound velocity $c_2$ in the liquid according to the formula $$c_2 = L(N/T_1 + N/T_2)/2$$

Concurrently with the determination of the sound velocity in the fluid and the flow velocity thereof, the density $\rho_2$ of the fluid is also determined. In the illustrated embodiment, this is done by means of the ultrasonic pulses $U_2$ in the countercurrent direction. When the piezoelectric crystal 5 shown in FIG. 2 emits an ultrasonic pulse $U_2$, this will in fact be propagated the distance $x_0$ through the first block 6 and encounter the second block 7. Since the two blocks consist of materials having different acoustic impedances $Z_0$ and $Z_1$, respectively, part of the ultrasonic pulse $U_2$ will be reflected in the boundary between the two blocks and again traverse the distance $x_0$ back to the crystal 5. The rest of the pulse will be transmitted into the second block. Similarly, part of the ultrasonic pulse transmitted into the second block 7 and propagated the distance $x_1$ will be reflected in the boundary between this block and the fluid and the rest of the pulse will be transmitted into the fluid. The part of the pulse which is reflected will again traverse the distance $x_1$ and encounter the boundary between the block 7 and the block 6, part of the pulse being reflected and the rest being transmitted into the block 6 and traversing the distance $x_0$ up to the crystal 5. The amplitude $A_{r1}$ of the ultrasonic pulse reflected in the boundary between the first and the second block 6, 7 and returned to the crystal 5, and the amplitude $A_{t2ra}$ of the ultrasonic pulse reflected in the boundary between the second block 7 and the fluid, transmitted through the boundary between the blocks 7 and 6 and returned to the crystal 5 are measured by means of the amplitude detector 12 and the A/D converter 11 and thereafter supplied to the microprocessor 10. Further, the periodic time meter 9 measures the time passing from the point of time the piezoelectric crystal 5 emits an ultrasonic pulse to the point of time it receives the ultrasonic pulse reflected from the first boundary and the ultrasonic pulse reflected from the second boundary, respectively. These times are supplied to the microprocessor 10 calculating the sound velocity $c_0$ in the first block 6 according to the formula $$c_0 = 2x_0/t_0$$

where $x_0$ is the length of the first block 6 and $t_0$ the time it takes the sound to traverse the distance $2x_0$, and the sound velocity $c_1$ in the second block 7 according to the formula $$c_1 = 2x_1/t_1$$

where $x_1$ is the length of the second block 7 and $t_1$ the time it takes the sound to traverse the distance $2x_1$.

The sound velocities $c_0$ and $c_1$ and the amplitudes $A_{r1}$ and $A_{t2r1}$ of the reflected ultrasonic pulses are used for calculating the density $\rho_2$ of the fluid. It is here on the fact that the acoustic impedance Z is dependent on the sound velocity c and the density $\rho$ according to the formula $$Z = \rho \times c$$

and that the reflection coefficient R for the reflection of an ultrasonic pulse in a boundary between two materials having different acoustic impedance is defined as the quotient of the amplitude $A_{r1}$ of the reflected pulse and the amplitude $A_0$ of the incident pulse, and is dependent on the acoustic impedances $Z_1$ and $Z_2$ of the two materials according to the formula $$R = A_{r1}/A_0 = (Z_2 - Z_1)/(Z_2 + Z_1) = (\rho_2 c_2 - \rho_1 c_1)/(\rho_1 c_1 + \rho_2 c_2) \quad (1)$$

Further, a transmission coefficient T is defined as $$T = A_{t1}/A_0 = 2\rho_2 c_2/(\rho_1 c_1 + \rho_2 c_2) \quad (2)$$

where $A_{t1}$ is the part of the incident pulse transmitted into the second material.

In the case of the transducer shown in FIG. 2, the following amplitude $A_{r1}$ is obtained for the ultrasonic pulse reflected in the boundary between the $$A_{r1} = \frac{\rho_1 c_1 - \rho_0 c_0}{\rho_0 c_0 + \rho_1 c_1} A_0 e^{-2ax0} \quad (3)$$

where $A_0$ is the amplitude of the incident ultrasonic pulse, $\rho_0$ and $\rho_1$ the density of the first and the second block, respectively, $c_0$ and $c_1$ the sound velocity in the first and the second block, respectively, and $e^{-2ax0}$ the attenuation which the ultrasonic pulse undergoes when it is propagated through the first block. The amplitude $A_{r1}$ can be measured by means of the ultrasonic transducer 4 and the amplitude detector 12. The transmitted part $A_{t1}$ of the incident ultrasonic signal becomes according to equation (2):

$$A_{t1} = \frac{2\rho_1 c_1}{\rho_0 c_0 + \rho_1 c_1} A_0 e^{-ax0} \quad (4)$$

Similarly, for the boundary between the second block and the fluid the amplitude $A_{t1r1}$ is obtained for the reflected part of the ultrasonic signal:

$$A_{t1r1} = \frac{\rho_2 c_2 - \rho_1 c_1}{\rho_1 c_1 + \rho_2 c_2} A_{t1} e^{-ax1} \quad (5)$$

The signal thus reflected thereafter encounters the boundary between the second and the first block. Here, the transmitted part $A_{t2r1}$ becomes:

$$A_{t2r1} = \frac{2\rho_0 c_0}{\rho_1 c_1 + \rho_0 c_0} A_{t1r1} e^{-ax1} \quad (6)$$

The amplitude $A_{t2r1}$, like the amplitude $A_{r1}$, can be measured by means of the transducer 4 and the amplitude detector 12. If equation 4 is inserted in equation 5 and equation 5 thereafter inserted in equation 6 and the obtained expression for $A_{t2r1}$ is divided by equation 3, an equation is obtained which is dependent upon the two measurable amplitudes $A_{t2r1}$ and $A_{r1}$ and upon the sound velocities in and the densities of the two blocks and the fluid:

$$A_{t2r1} = \frac{\rho_2 c_2 - \rho_1 c_1}{\rho_1 c_1 + \rho_2 c_2} \frac{4\rho_0 c_0 \rho_1 c_1}{(\rho_1 c_1)^2 - (\rho_0 c_0)^2} A_{r1} e^{-2ax_1} \quad (7)$$

By equation 7, an expression can be obtained for the density $\rho_2$ of the fluid, which becomes:

$$\rho_2 = \frac{\rho_1 c_1}{c_2} \frac{4\rho_0 c_0 \rho_1 c_1 A_{r1} e^{-2ax_1} - (\rho_0^2 c_0^2 - \rho_1^2 c_1^2) A_{t2r1}}{4\rho_0 c_0 \rho_1 c_1 A_{r1} e^{-2ax_1} + (\rho_0^2 c_0^2 - \rho_1^2 c_1^2) A_{t2r1}} \quad (8)$$

As previously mentioned, the values for $c_0$ and $c_1$ can be obtained by pulse-echo-transit time measurements according to the formula:

$$c_i = \frac{2x_i}{t_i} \quad (9)$$

where i is equal to 0:1. Further, the sound velocity $c_2$ in the fluid as above can be obtained by the sing-around method, where $$c_2 = \frac{L}{2}\left(\frac{N}{T_1} + \frac{N}{T_2}\right) \quad (10)$$

If equations 9 and 10 are inserted in equation 8, the following equation is obtained:

$$\rho_2 = \frac{4\rho_1 x_1}{L\left(\frac{N}{T_1} + \frac{N}{T_2}\right)t_1} \frac{\frac{16\rho_0 \rho_1 x_0 x_1}{t_0 t_1} A_{r1} e^{-2ax_1} - \left(\frac{4\rho_0^2 x_0^2}{t_0^2} - \frac{4\rho_1^2 x_1^2}{t_1^2}\right) A_{t2r1}}{\frac{16\rho_0 \rho_1 x_0 x_1}{t_0 t_1} A_{r1} e^{-2ax_1} + \left(\frac{4\rho_0^2 x_0^2}{t_0^2} - \frac{4\rho_1^2 x_1^2}{t_1^2}\right) A_{t2r1}} \quad (11)$$

This equation contains six momentarily measurable parameters ($T_1$, $T_2$, $t_0$, $t_1$, $A_{r1}$ and $A_{t2r1}$) which all vary with flow, density, pressure, temperature, ageing etc, and seven parameters (N, L, $x_0$, $x_1$, $\rho$, $\rho_1$, a) which are dependent only on the construction of the apparatus and can be determined in advance. From this appears that all parameters which can vary with the measuring conditions are measured when determining the mass flow, whereby an accurate measuring value can be obtained.

Thus, the microprocessor 10 determines the density $\rho_2$ of the fluid according to formula 11 above, and the mass flow M of the fluid can then be determined according to the formula $$M = \rho_2 \times A \times V.$$

To simplify measurements, the acoustic impedance $Z_2$ of the fluid should preferably be less than the acoustic impedance $Z_1$ of the second block 7, which in turn should be less than the acoustic impedance $Z_0$ of the first block 6.

Further, the pulse time $t_{p0}$ of the ultrasonic pulse emitted from the piezoelectric crystal 5 in the transducer 4 should be shorter than the time it takes the ultrasonic pulse to travel through the first block and back again, i.e. $t_{p0} < 2x_0/c_0$; otherwise the reflected pulse cannot be distinguished from the emitted pulse.

The method and the apparatus for measuring mass flows have been described above in one embodiment. However, it is obvious to those skilled in the art that the method and apparatus described above can be varied in several different ways within the scope of the accompanying claims. For example, the transducer for measuring the density of the fluid may instead be disposed in the upstream end of the pipe section. Alternatively, both transducers 3 and 4 may be designed for density measurement.

Further, the transducers need not be disposed in opposite ends of a pipe section, but may instead be disposed on the periphery of the pipe section obliquely opposite each other in such a manner that velocity vector of the ultrasonic signal will have one component in the flow direction of the fluid when the ultrasonic signal is propagated from one transducer to the other. In this case, the cocurrent/countercurrent direction of the fluid is defined as all the directions in which the velocity vector of the ultrasonic signal has one component in the cocurrent/countercurrent direction of the fluid. Further, the formula for the flow velocity v of the fluid becomes:

$$v = L(N/T_1 - N/T_2)/2 \cos\theta$$

where $\theta$ is the angle between the longitudinal axis of the pipe and the direction of propagation of the ultrasonic signal. In the embodiment shown in the Figures, $\theta = 0°$ and, thus, $\cos\theta = 1$.

Instead of two ultrasonic transducers it is possible to use three or more transducers, e.g. two transducers for the sing-around measurement and one transducer for determination of density.

Further, the use of a U-shaped pipe is not compulsory, but the transducers may be mounted in or on the periphery of e.g. a straight pipe.

I claim:

1. Method for measuring the mass flow M of a fluid flowing through a pipe having a cross-sectional area A, said method comprising
    a) causing an ultrasonic pulse ($U_1$) to traverse a distance (L) in the cocurrent direction of the fluid N times, where N is greater than or equal to 1;
    b) measuring the time ($T_1$) it takes the ultrasonic pulse ($U_1$) to traverse said distance (L) in the cocurrent direction of said fluid N times;
    c) causing an ultrasonic pulse ($U_2$) to traverse said distance (L) in the countercurrent direction of said fluid N times;
    d) measuring the time ($T_2$) it takes the ultrasonic pulse ($U_2$) to traverse said distance (L) in the countercurrent direction of said fluid N times;
    e) determining the flow velocity (v) of said fluid as $$v = L \, (N/T_1 - N/T_2)/2 \cos\theta$$

where $\theta$ is the angle between the longitudinal axis of the pipe and the direction of propagation of said ultrasonic pulse ($U_1$ or $U_2$), f) determining the sound velocity ($c_2$) in said fluid as $$c_2 = L \, (N/T_1 + N/T_2)/2$$

g) causing an ultrasonic pulse ($U_1$, $U_2$) to traverse a distance $x_0$ in a first material having a density $\rho_0$ and thereafter a distance $x_1$ in a second material having a density $\rho_1$, before being caused to traverse said fluid;

h) determining the sound velocity $c_0$ and $c_1$ in said first and said second material, respectively;

i) measuring the amplitude $A_{r1}$ of a part of said ultrasonic pulse ($U_1$, $U_2$) which is reflected in a boundary between said first and said second material and which thereafter again traverses the distance $x_0$ in said first material;

j) measuring the amplitude $A_{t2r1}$ of a part of said ultrasonic pulse ($U_1$, $U_2$) which is reflected in a boundary between said second material and said fluid and which thereafter again traverses the distance $x_1$ in said second material and the distance $x_0$ in said first material;

k) determining the density $\rho_2$ of the fluid as $$\rho_2 = \frac{\rho_1 c_1}{c_2} \left( \frac{4\rho_0 c_0 \rho_1 c_1 A_{r1} e^{-2\alpha x_1} - (\rho_0^2 c_0^2 - \rho_1^2 c_1^2) A_{t2r1}}{4\rho_0 c_0 \rho_1 c_1 A_{r1} e^{-2\alpha x_1} + (\rho_0^2 c_0^2 - \rho_1^2 c_1^2) A_{t2r1}} \right) \quad (8)$$

l) determining the mass flow M of said fluid as $M = v \times A \times \rho_2$.

2. Method as claimed in claim 1, where N is equal to 1, wherein steps a-d are repeated P times, where P is greater than or equal to 1, the mean of said times in said cocurrent and countercurrent directions, respectively, is formed and the mean times are used for the calculation of the flow velocity v of the fluid and the sound velocity $c_2$ therein.

3. Method as claimed in claim 1, wherein the velocity $c_0$ in said first material is measured by measuring the time $t_0$ it takes the ultrasonic pulse ($U_1$, $U_2$) to traverse the distance $2x_0$, the sound velocity being obtained as $c_0 = 2x_0/t_0$.

4. Method as claimed in claim 3, wherein the sound velocity $c_1$ in said second material is measured by measuring the time $t_1$ it takes the ultrasonic pulse ($U_1$, $U_2$) to traverse the distance $2x_1$, the sound velocity $c_1$ being obtained as $c_1 = 2x_1/t_1$.

5. Apparatus for measuring the mass flow M of a fluid having an acoustic impedance $Z_2$, comprising two means (3, 4) for transmitting and receiving ultrasonic pulses, said means being located opposite each other and at a distance L from each other in a pipe section having a cross-sectional area A, time metering means (9) for measuring the time it takes an ultrasonic pulse to traverse said distance L in the fluid N times, where N is greater than or equal to 1, calculating means (10) for calculating the flow velocity v of the fluid, and means for measuring the density $\rho_2$ of the fluid, wherein said means for measuring the density $\rho_2$ comprises a first block (6) of a material having an acoustic impedance $Z_0$ is disposed adjacent one of said means (3, 4) for transmitting and receiving ultrasonic pulses, a second block (7) of a material having an acoustic impedance $Z_1$ is disposed between said first block (6) and the fluid, and amplitude metering means (12) for measuring the amplitude of ultrasonic pulses which have been reflected in the boundary between said first and said second block and between said second block and the fluid, and that the apparatus further comprises calculating means (10) for calculating the sound velocity $c_2$ in the fluid on the basis of the times measured by said time metering means, the density $\rho_2$ of the fluid on the basis of the sound velocity $c_2$, the acoustic impedances $Z_0$ and $Z_1$, and the amplitudes measured by said amplitude metering means (12), as well as the mass flow M according to the formula $M = \rho_2 \times A \times v$, are included.

6. Apparatus as claimed in claim 5, wherein means (9) for measuring the sound velocity $c_0$ and $c_1$ in said first and said second material, respectively are included.

7. Apparatus as claimed in claim 5, wherein the acoustic impedance $Z_2$ of the fluid is less than the acoustic impedance $Z_1$ of said second block (7), which is less than the acoustic impedance $Z_0$ of said first block (6).

8. Apparatus as claimed in claim 5, wherein said one means for transmitting and receiving ultrasonic pulses is adapted to transmit ultrasonic pulses, the pulse length of which is shorter than $2 x_0/c_0$, where $x_0$ is the length of said first block (6).

9. Apparatus as claimed in any one of claim 5, wherein said one means for transmitting and receiving ultrasonic pulses is disposed in the downstream end of said pipe section (2).

* * * * *

UNITED STATES PATENT AND TRADEMARK OFFICE
CERTIFICATE OF CORRECTION

PATENT NO. : 5,214,966
DATED : June 1, 1993
INVENTOR(S) : Jerker Delsing

It is certified that error appears in the above-identified patent and that said Letters Patent is hereby corrected as shown below:

Cover page, Item [22], delete "1991" and substitute therefor --1989--.

Signed and Sealed this

Eleventh Day of January, 1994

Attest:

BRUCE LEHMAN

*Attesting Officer*   *Commissioner of Patents and Trademarks*